United States Patent [19]
Lanks

[11] Patent Number: 6,020,316
[45] Date of Patent: Feb. 1, 2000

[54] GLUTARALDEHYDE MODIFIED CHEMOTHERAPEUTIC AGENTS AND METHODS OF USE THEREOF

[76] Inventor: Karl W. Lanks, 824 President St., New York, N.Y. 11215

[21] Appl. No.: 09/160,819

[22] Filed: Sep. 25, 1998

Related U.S. Application Data

[60] Provisional application No. 60/060,026, Sep. 25, 1997.
[51] Int. Cl.⁷ .............................. A61K 31/70; C07H 1/00; C07H 15/24
[52] U.S. Cl. .............................. 514/34; 536/6.4; 536/18.5
[58] Field of Search ...................................... 536/6.5, 18.5; 514/34

[56] References Cited

U.S. PATENT DOCUMENTS

| | | | |
|---|---|---|---|
| 4,202,967 | 5/1980 | Tong et al. | 536/6.4 |
| 4,460,560 | 7/1984 | Tokes et al. | 424/1.1 |
| 4,625,019 | 11/1986 | Relyveld | 536/6.4 |
| 5,208,323 | 5/1993 | Pase et al. | 530/391.9 |

*Primary Examiner*—Elli Peselev
*Attorney, Agent, or Firm*—Darby & Darby

[57] ABSTRACT

Clinical utility of chemotherapy agents is limited by dose-dependent systemic toxicity and emergence of resistant tumor cell lines. The present invention provides derivatives of chemotherapeutic agents which can overcome these limitations. Reaction of a parent drug with glutaraldehyde in aqueous solution followed by ethanolamine yields a product which exhibits enhanced antitumor cytotoxicity and overcomes resistance developed against the parent drug. The derivative compounds of the invention achieve therapeutic effects comparable to those of the parent drugs but at much lower doses, thereby reducing undesirable toxic side effects. The most preferred derivative is glutaraldehyde-modified doxorubicin. Most preferred are methods of treatment for subjects suffering from cancer which comprise administration of glutaraldehyde-modified doxorubicin.

19 Claims, 7 Drawing Sheets

GLUTARALDEHYDE MODIFIED CHEMOTHERAPEUTIC AGENTS AND METHODS OF USE THEREOF

This application claims benefit of U.S. Provisional 60/060,026 filed Sep. 25, 1997.

FIELD OF THE INVENTION

This application relates generally to the treatment of cancer. Specifically, the invention relates to novel glutaraldehyde-modified compounds useful for chemotherapy, methods of synthesis of these compounds, and methods of treatment employing these compounds.

BACKGROUND OF THE INVENTION

Most of the cancer chemotherapy agents currently in clinical use are cytotoxins. That is, they kill cancer cells by interfering with cell division, e.g., by damaging the DNA of dividing cells, or by inhibiting the production of the deoxynucleotides that are necessary to replicate DNA during cell division. The usefulness of most cancer chemotherapeutic agents is limited by their systemic toxicity and, in many cases, the development of resistant tumor cells.

An example of such a chemotherapeutic agent is doxorubicin. Although doxorubicin is an effective and widely used cancer chemotherapeutic agent, its clinical utility is significantly limited by a dose-dependent cardiotoxicity and the frequent emergence of resistant tumor cells. One approach to circumventing these limitations has been to increase antitumor cytotoxicity by coupling the drug to various carriers such as monoclonal antitumor antibodies (Diener E, Diner U E, Sinha A, Xie S, Verdigis R (1986) *Science* 231: 148), albumin (Hatano T, Ohkawa K, Matsuda M (1993) *Tumor Biol.* 14: 288; Gabor F, Wollmann K, Theyer G, Haberl I, Hamilton G (1994); *Anticancer Res.* 14: 1943), and transferrin (Berczi A, Barabas K, Sizensky J A, Faulk W P (1993) *Arch. Biochem. Biophys.* 300: 356; Fritzer M, Barabas K, Szuts V, Berczi A, Szekeres T, Faulk W P, Goldenberg H (1992) *Int. J. Cancer* 52: 619; Faulk W P, Taylor C G, Yeh C G, McIntyre J A (1990) *Mol. Biother.* 2: 57; Thorstensen K, Romslo I (1993) *Scand. J. Clin. Lab. Invest.* 53 (Suppl 215): 113). These strategies have aimed to decrease the clinically effective dosage of the drug and, thereby, to lessen undesirable side effects such as cardiac toxicity. Crosslinking doxorubicin to transferrin has been found to yield preparations with enhanced cytotoxicity (Lai B-T, Gao J-P and Lanks K W (1997) *Cancer Chemother. Pharmacol.*).

The present invention provides for the synthesis of glutaraldehyde modified doxorubicin and other glutaraldehyde-modified chemotherapeutic agents. The glutaraldehyde modified compounds of the invention have a predicted structure, based on the method used to synthesize them and the known reactivity of the reagents used in the method, of R—NH—CO—$(CH_2)_3$—CO—NH$(CH_2)_2$OH, where R—NH— is the portion of the derivative compound comprising the parent compound.

Various modifications of doxorubicin with glutaraldehyde have been reported in the prior art. A doxorubicin derivative where the terminal aldehyde group was not blocked with ethanolamine was prepared by Page et al., U.S. Pat. No. 5,208,323, but the antitumor efficacy of this compound was not evaluated. Glutaraldehyde-crosslinked polymers of daunorubicin have been prepared by Relyveld, U.S. Pat. No. 4,625,019, and appear to have antitumor activity upon spontaneous hydrolysis. However, the compounds produced by Relyveld are not synthesized by the method used to produce the derivatives of the present invention. Tong et al., in U.S. Pat. No. 4,202,967, produced a N,N-pentamethylene derivative of doxorubicin by reaction of glutaraldehyde with doxorubicin. This reaction is done without subsequent addition of ethanolamine, and results in a cyclic pentamethylene adduct. Further, the compounds disclosed by Tong, et al. exhibited antitumor activities that were decreased about four-fold, on a weight basis, relative to the parent doxorubicin or daunorubicin compound. Thus, there remains a need in the art for glutaraldehyde-modified chemotherapeutic agents, and particularly glutaraldehyde-modified anthracyclines such as doxorubicin, that display antitumor efficacy at lower doses than the parent compounds. There is also a need in the art for chemotherapeutic agents that are effective against tumor cells that have attained resistance against conventional, or unmodified, chemotherapeutic agents.

SUMMARY OF THE INVENTION

The present inventor has now surprisingly and unexpectedly discovered that reaction of chemotherapeutic agents that possess a reactive amine group with glutaraldehyde alone, without conjugation to any protein, yields derivatives of the chemotherapeutic agents that are more potent against tumor cells than the parent drugs. The glutaraldehyde derivatized compounds are also effective against tumors that have developed resistance to the parent compounds.

Thus, in one aspect, the present invention is directed to the reaction product of glutaraldehyde and a cancer chemotherapeutic agent that possesses a reactive amine group.

In another aspect, the present invention is directed to methods for treating tumors which comprise administering an effective amount of a glutaraldehyde-modified cancer chemotherapeutic agent to a subject suffering from a tumor.

In another aspect, the invention is directed to the reaction product of glutaraldehyde and a member of the anthracycline group of cancer chemotherapeutic agents that possess reactive amine groups, nonlimiting examples of which are daunorubicin and doxorubicin.

In yet another aspect, the invention is directed to methods for treating tumors which comprise administering an effective amount of a glutaraldehyde-modified anthracycline cancer chemotherapeutic agent to a subject suffering from a tumor.

In a further aspect, the present invention is directed to the reaction product of glutaraldehyde and doxorubicin, and to methods for treating tumors which comprise administering an effective amount of glutaraldehyde-modified doxorubicin to a subject suffering from a tumor.

The present invention also relates to synthetic methods for modifying chemotherapeutic agents with glutaraldehyde to provide derivatives with increased toxicity against cancer cells, and to provide derivatives that are effective against tumors that are resistant to the parent agent.

DETAILED DESCRIPTION OF THE INVENTION

Figure 1:
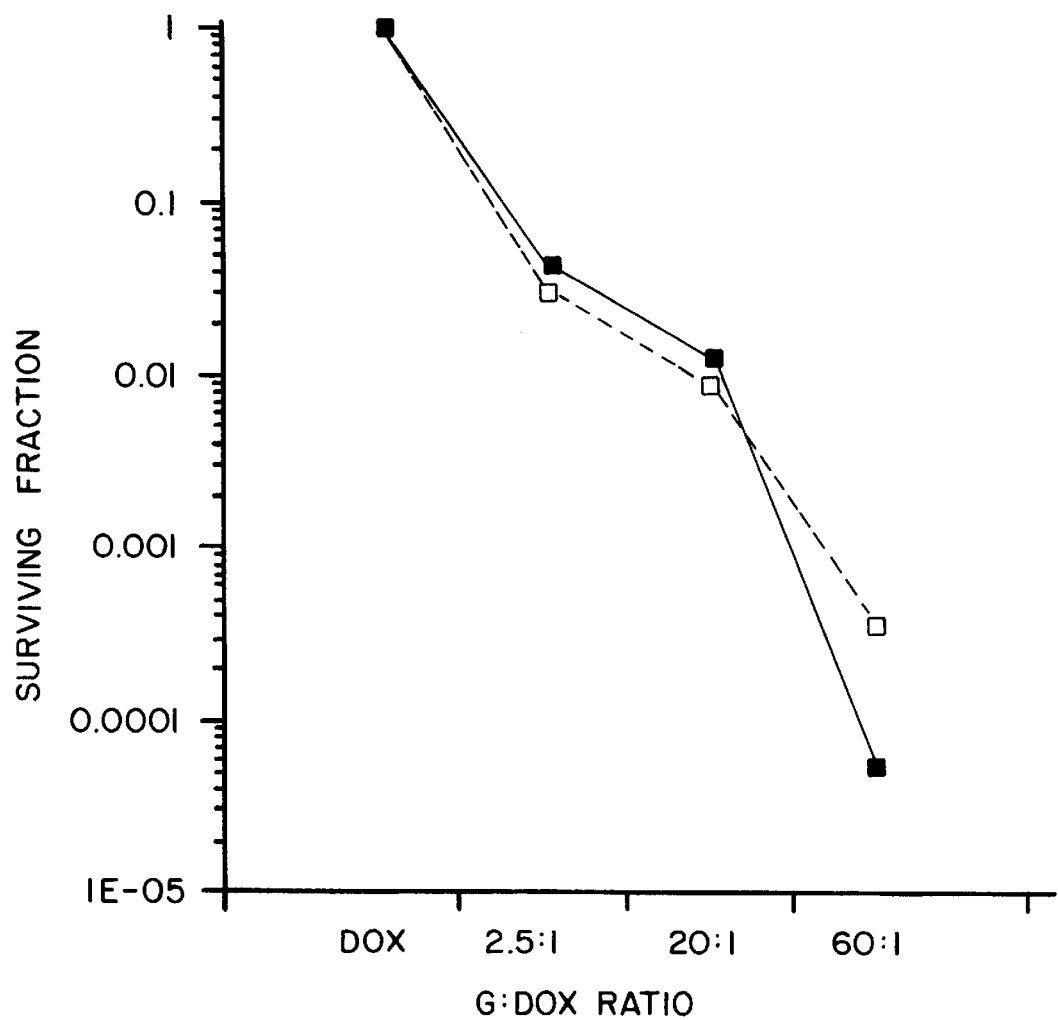
FIG. 1 is a graph that illustrates the effect of GLU-DOX (glutaraldehyde-modified doxorubicin) on clonogenic survival of cultured unselected (■—■) and doxorubicin-resistant (□----□) L929 cells.

All patents, patent applications, and publications referred to in this specification are herein incorporated by reference in their entirety. In case of a conflict between the present disclosure and a document incorporated by reference, the present disclosure controls.

The cancer chemotherapeutic agent derivatives of the invention are prepared by the incubation of reactive amine-containing parent chemotherapeutic agents with glutaraldehyde at about room temperature. The ratio of glutaraldehyde to chemotherapeutic agent typically ranges from 2.5:1 to 500:1, preferably about 100:1. The concentration of glutaraldehyde typically will range from 10 to 500 mM. The cancer chemotherapeutic agent is typically present in the reaction mixture at a concentration of between 0.5 and 5 mM, preferably about 1 mM. The reactions are allowed to proceed for between 1 minute and 1 hour, preferably between 3 and 10 minutes, and most preferably about 4 minutes. The reactions are conducted in an aqueous solution or organic solvent in which both glutaraldehyde and the agent of interest are soluble. It is preferable to conduct the reactions in an aqueous sodium chloride solution at pH 7. The concentration of sodium chloride in the reaction can be between about 10 mM and about 1M, preferably between about 100 and about 500 mM, and is most preferably about 150 mM.

After incubation of the chemotherapeutic agent and glutaraldehyde, ethanolamine HCl is added. Ethanolamine is believed to react with the aldehyde moiety of glutaraldehyde that has not reacted with the amine moiety of the chemotherapeutic agent. The concentration of ethanolamine typically employed in the reaction mixture is 5 to 100 mM, preferably about 7 mM.

Chemotherapeutic agents suitable for modification with glutaraldehyde include those with free, reactive amino groups. Preferred chemotherapeutic agents are anthracycline antibiotic chemotherapeutic agents. Several thousand anthracycline derivatives have been obtained either from streptomyces biosynthesis or via the semisynthetic modification of known natural anthracycline antibiotics (Arcamone, F., *Doxorubicin*, Academic Press, New York 1980; Thomson, R. H., *Naturally Occurring Quinones III: Recent Advances*, Chapman and Hall, New York 1987; *Anthracyclines: Current Status and New Developments*, Academic Press, New York, 1980; Brown, J. R. and Iman, S. H., *Recent Studies on Doxorubicin and its Analogues, Prog. Med. Chem.* 21 170–236, 1984; Brown, J. R. *Adriamycin and Related Anthracycline Antibiotics, Prog. Med. Chem.*, 15, 125–164, 1978). The majority of known anthracyclines show two types of structural differences: (i) the substitution pattern of the aglycone tetracyclic ring system, and (ii) the structure and number of glycosides attached at C-7 or C-10 (doxorubicin numbering). Preferred compounds of the present invention are glutaraldehyde-modified doxorubicin, daunorubicin, idarubicin, epirubicin, esorubicin, iododoxorubicin, and pirarubicin. The most preferred compounds of the present invention are glutaraldehyde-modified daunorubicin and doxorubicin. The preferred and most preferred compounds of the invention are also preferred and most preferred in the practice of the methods of the present invention, respectively.

Glutaraldehyde-modified chemotherapeutic agents can be purified by standard chromatography methods known to those of ordinary skill in the art, for example, normal chromatography on silica gel, high pressure liquid chromatography, or reversed phase liquid chromatography.

The present invention also provides a method of treating tumors in mammalian subjects, comprising administering to a mammal having a tumor an effective amount of a glutaraldehyde-modified cancer chemotherapeutic agent, or a pharmaceutically acceptable addition salt thereof.

The term "effective amount" as used herein, means an amount of a compound of the present invention which is capable of stopping, slowing, or reversing tumor growth and is not lethal to the recipient thereof. The specific dose of compound administered according to this invention will, of course, be determined by the particular circumstances surrounding the case, including, for example, the compound administered, the route of administration, and the condition being treated. Typically, doses of glutaraldehyde-modified agents of the invention will be about 50 times less than the dose of the parent agent. Administration regimens, i.e., the frequency and timing of administration of the glutaraldehyde-modified chemotherapeutic agents of the invention, will typically be the same as the parent drugs.

A typical dose of the GLU-DOX composition of the present invention is between about 0.1 mg and about 10 mg per square meter of a patient's surface area, preferably between about 1 and about 3 mg per square meter of a patient's surface area. When administered intravesically, as in the treatment of, e.g., bladder cancer, the typical dose is between about 0.1 mg and about 10 mg, preferably between about 1 and about 3 mg. Such intravesical dosages are typically administered about every 3 weeks for 4 to 8 administration cycles. When administered intravenously, the GLU-DOX is administered in cycles of from about 3 to about 4 weeks, depending on the subject's tolerance to treatment.

The compounds of the invention can be administered by a variety of routes including oral, subcutaneous, intravenous, intramuscular, intraperitoneal, and by direct application to an affected organ.

Preferably, the compounds are formulated prior to administration. These pharmaceutical formulations comprise an effective amount of a glutaraldehyde-modified chemotherapeutic agent, or a pharmaceutically acceptable salt thereof in association with a pharmaceutically acceptable carrier, diluent or excipient therefor.

The active ingredient in such formulations comprise from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, propylhydroxybenzoates, talc, magnesium stearate and mineral oil. The formulations may additionally include lubricating agents, wetting agents, emulsifying agents, suspending agents, preserving agents, sweetening agents, flavoring agents, and the like. The compositions may be formulated so as to provide quick, sustained or delayed release of the active ingredient after administration to the patient by employing procedures well known in the art.

The invention can be better understood by reference to the following examples, which are illustrative only and are not meant to limit the scope of the invention in any way.

EXAMPLE 1

Synthesis of GLU-DOX

In the following Example, and in all other Examples, the abbreviation DOX is used for unmodified doxorubicin, and GLU-DOX is used when referring to glutaraldehyde-modified doxorubicin.

279 $\mu$l of glutaraldehyde (215 mM in 150 mM NaCl at 25° C.) was added dropwise with stirring to 171 $\mu$l of doxorubicin (2 mg/ml in 150 mM NaCl at 25° C.) and 150 $\mu$l of water. After incubation for 4 minutes at 25° C., 160 $\mu$l of ethanolamine HCl (37.2 mM in 150 mM NaCl, pH 8.0) was added and the mixture was incubated an additional 4 minutes at 25° C. The clear supernatant resulting from the reaction was centrifuged at 2,500×g for 10 minutes at 4° C. and was stored at 4° C. and used in subsequent experiments. The yield was 33 percent based on the absorbance of the solution at 488 nm and the extinction coefficient of DOX at that wavelength.

Other aldehydes and crosslinking agents that were substituted for glutaraldehyde in the basic modification protocol included acetaldehyde, butyraldehyde, hexanal, formaldehyde, succinyl chloride, glutaryl dichloride (all from Aldrich Chemical Co., Milwaukee, Wis.), DSG (disuccinimidyl glutarate), DMS (dimethylsuberimidate), and BS[3] (last three compounds from Pierce Chemical Co., Rockford, Ill.). None of these compounds, when reacted with DOX, produced a derivative with increased antitumor cell activity relative to DOX.

EXAMPLE 2

Evaluation of Tumor Cell Cytotoxic Activity

The murine L929 cell line, a human breast adenocarcinoma cell line (MCF-7) and a human bladder transitional cell carcinoma cell line (RT-4) were used to test the compounds of the present invention. All cell lines were obtained from MA Bioproducts (Bethesda, Md.) and were routinely maintained in high-glucose Dulbecco's Modified Eagle's Minimum Essential Medium (DMEM) and 10% newborn calf serum (L929) or 10% fetal calf serum (MCF-7 and RT-4). A DOX-resistant cell line, L929/DOX, was prepared by treating the L929 cell line with gradually increasing concentrations of DOX in vitro until a cell line that grew at a concentration of 50 $\mu$g/ml DOX was attained. A resistant subclone was then treated once with 100 $\mu$g/ml of DOX. The surviving resistant population was used in subsequent experiments. The L929/DOX cells were maintained in DMEM medium supplemented with 10% fetal calf serum and lacking DOX. Drug efflux data indicated that DOX was pumped out of the L929/DOX cells much faster than out of the wild type cells, consistent with a multidrug resistant phenotype.

Cells from the stock cultures were plated in 35 mm plastic tissue culture dishes at a density of 1×10$^5$/cm$^2$. After 1 to 2 days, when the monolayer had reached a final density of 2–3×10$^5$/cm$^2$, the cultures were washed twice with Dulbecco's phosphate-buffered saline and 2 ml of serum-free DMEM was added. After maintenance for 3 days with daily medium changes, DOX or GLU-DOX were added directly into the culture medium from concentrated stock solutions. Cultures were exposed to 0.1 $\mu$g/ml DOX or GLU-DOX prepared at the indicated glutaraldehyde:DOX molar ratio. After incubation for 3 hours at 37° C. in 10% CO$_2$, the dishes were rinsed twice with phosphate-buffered saline (pH 7.4) to remove extracellular drugs, trypsinized, and plated for determination of clonogenic survival. Trypsinization involved dispersal of cells with 0.25% trypsin, followed by culture in DMEM plus 10% newborn calf serum for 7 days. Plates were examined after staining with methylene blue, and clones containing more than 10 cells were counted. The surviving fraction was the ratio of the plating efficiency of the cultures exposed to DOX divided by the plating efficiency of control cultures maintained in a medium of the same composition. Plating efficiency is defined as the number of colonies formed divided by the number of cells plated. All experiments were performed from two to four times with similar results. The clonogenic survival assay was routinely accurate to ±20%.

Figure 2:
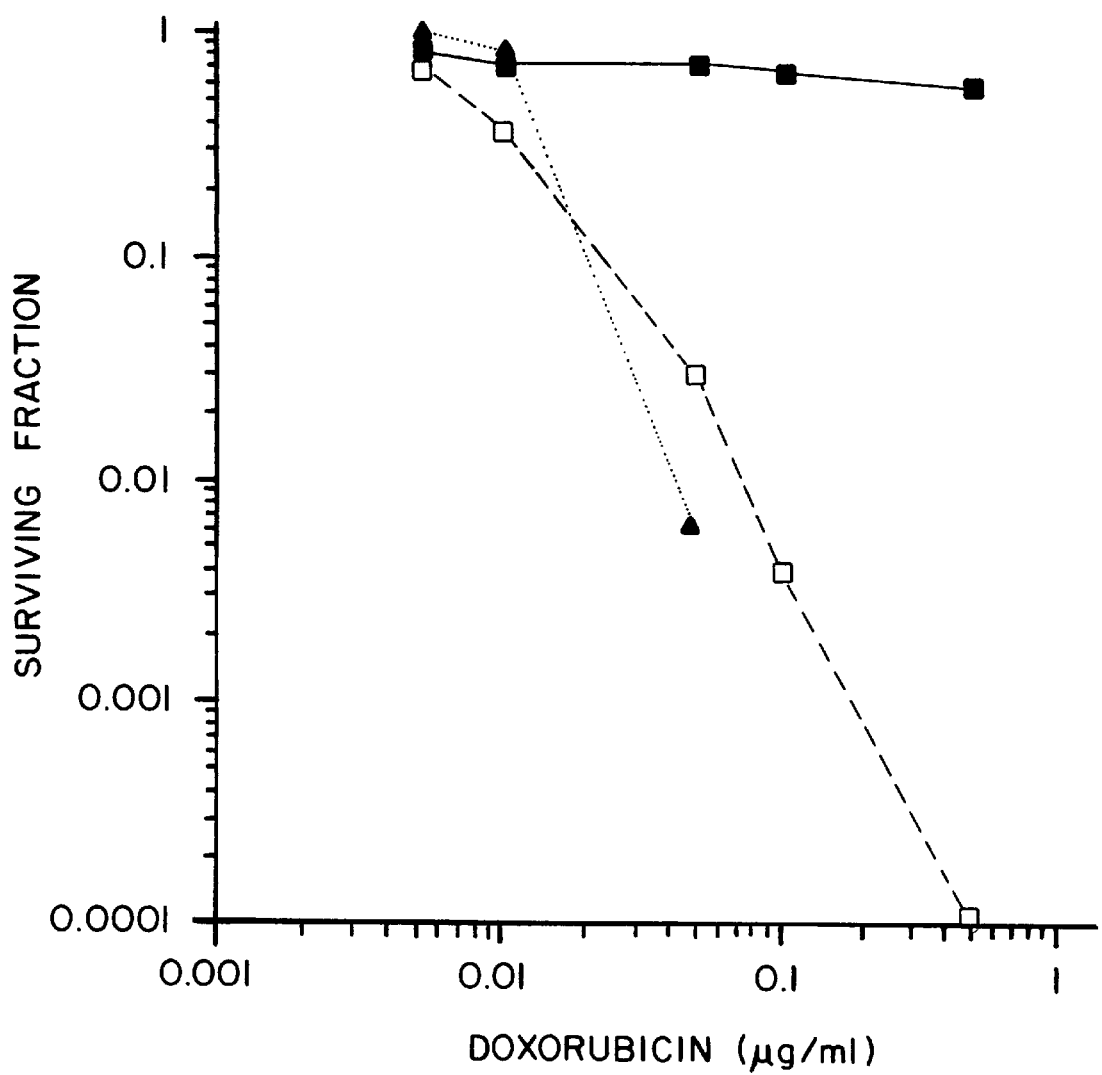
FIG. 2 is a graph that depicts the effect of DOX (■—■) and GLU-DOX (□-----□) on clonogenic survival of cultured L929 cells. GLU-DOX was prepared at 2.5:1 glutaraldehyde:DOX molar ratio. Survival data for a transferrin-DOX conjugate (▲—▲) are shown for comparison.

FIG. 1 shows that reaction of glutaraldehyde alone with DOX (2.5:1 to 60:1 molar ratio glutaraldehyde:DOX) in the absence of any protein yielded an adduct that was highly cytotoxic toward both the stock L929 cell line and its DOX-resistant derivative. Neither other mono- or bifunctional aldehydes nor several amino-reactive crosslinking agents increased DOX cytotoxicity when reacted at a 2.5:1 molar ratio. A more detailed dose-response analysis (FIG. 2) comparing DOX with GLU-DOX prepared at 2.5:1 glutaraldehyde DOX molar ratio shows that the cytotoxicity of the 2.5:1 product at the 0.05 μg/ml is increased ≈100-fold relative to unmodified DOX. This increase in cytotoxicity is very similar to that of glutaraldehyde-crosslinked DOX-transferrin conjugates prepared by the same procedure and this previously published data is overlaid on the present figure to facilitate comparison.

Figure 3A:
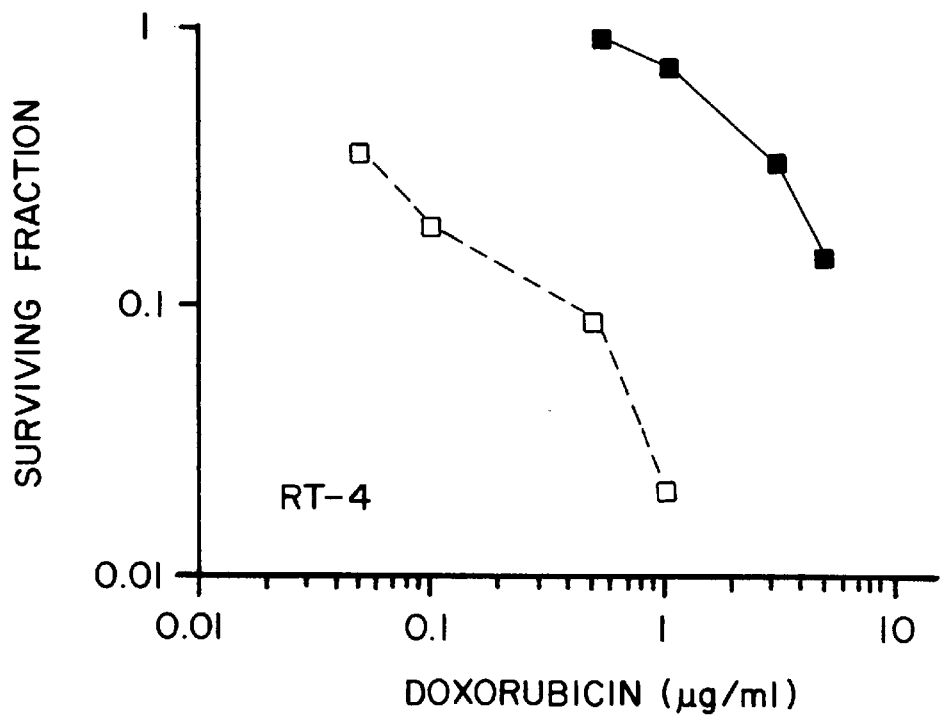
FIG. 3A is a graph showing the effect of DOX (■—■) and GLU-DOX (□-----□) on clonogenic survival of cultured human carcinoma cell line RT-4. GLU-DOX was prepared at 2.5:1 glutaraldehyde:DOX molar ratio.
Figure 3B:
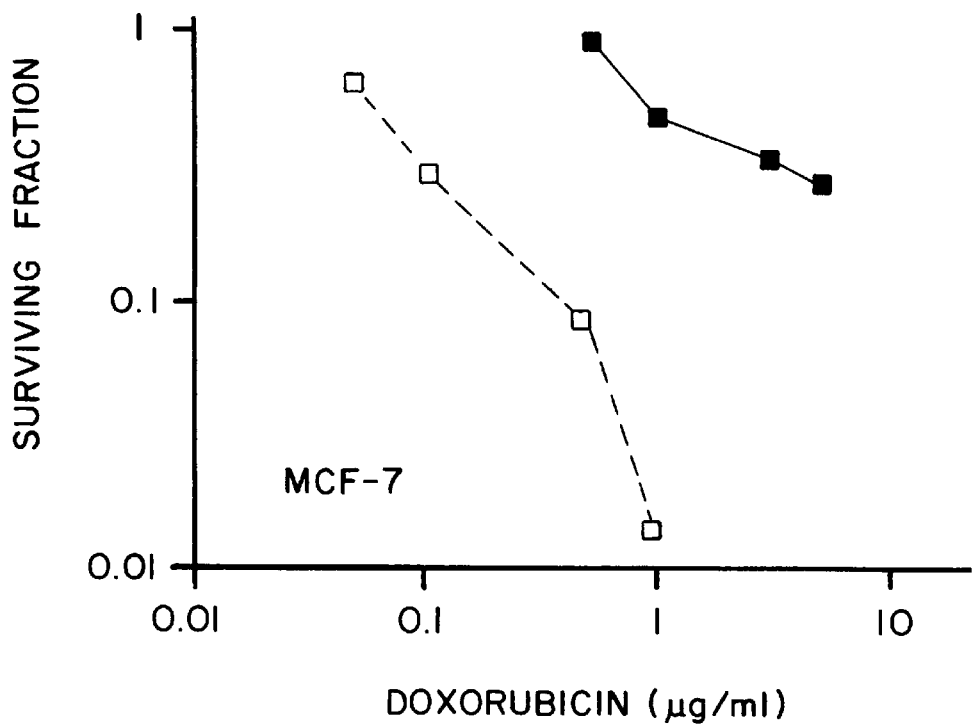
FIG. 3B is a graph showing the effect of DOX (■—■) and GLU-DOX (□-----□) on clonogenic survival of cultured human carcinoma cell line MCF-7. GLU-DOX was prepared at 2.5:1 glutaraldehyde:DOX molar ratio.
Figure 3C:
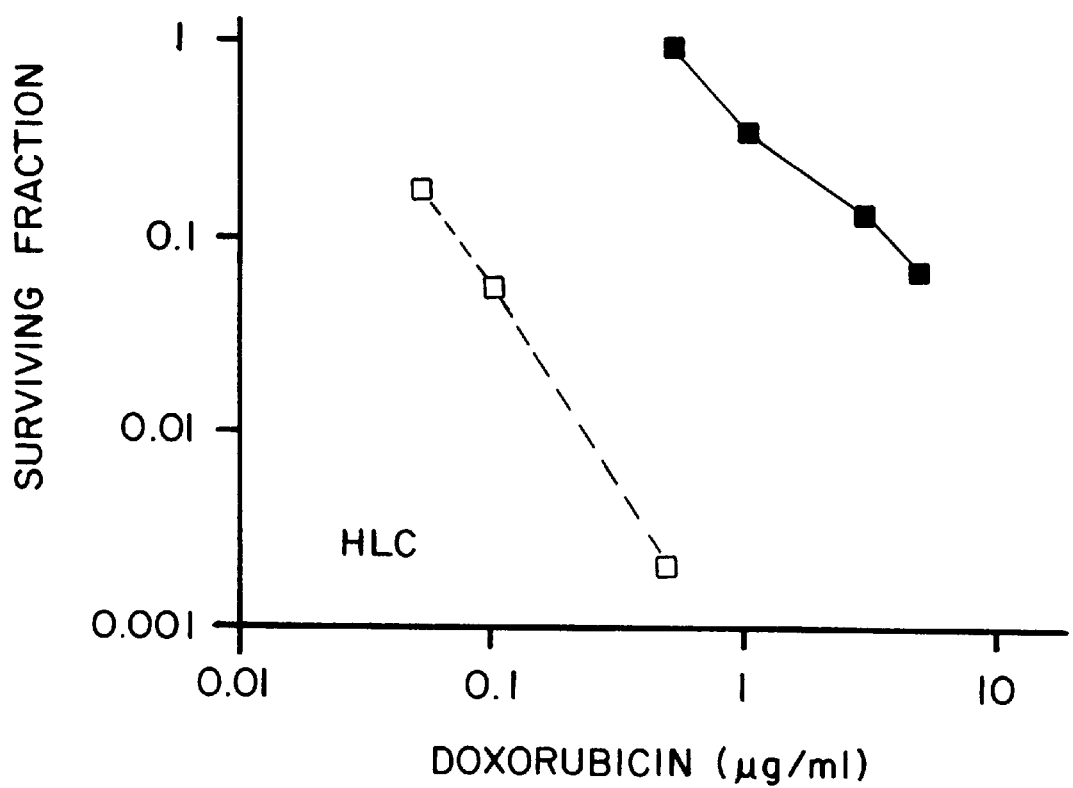
FIG. 3C is a graph showing the effect of DOX (■—■) and GLU-DOX (□-----□) on clonogenic survival of cultured human carcinoma cell line HLC. GLU-DOX was prepared at 2.5:1 glutaraldehyde:DOX molar ratio.

FIGS. 3A to 3C depict the results of similar experiments employing three human tumor cell lines: HTB (bladder transitional cell carcinoma, FIG. 3A), MCF-7 (breast adenocarcinoma, FIG. 3B), and HLC (lung carcinoma, FIG. 3C). Even though these lines are relatively insensitive to DOX, they were 10- to 100-fold more sensitive to GLU-DOX and at higher doses than those shown in the figure no clonogenic cells could be detected. In contrast with the response to DOX, the non-replicating cells did not persist as polyploid giant cells (Lanks, K W and Lehman, J M, *Cancer Research* 50:4776 (1990)). Rather, they appeared pyknotic and metabolically dead within 24–48 hr of exposure to GLU-DOX.

EXAMPLE 3

Fluorescence Localization of DOX and GLU-DOX in Tumor Cells

Cells were grown on 25 mm diameter microscope cover slips (Thomas, Sweedsboro, N.J.) in 35 mm tissue culture dishes. DOX, GLU-DOX or rhodamine 123 (Eastman Kodak, Rochester, N.Y.) were added to the wells and incubated for 3 h at 37° C. The wells were then rinsed two times with phosphate buffered saline and changed to fresh medium. After incubation for 0 h or 2 h, the cover slips were extracted from the plates, rinsed with PBS, mounted in an Attofluor cell chamber (Molecular Probes, Inc. Eugene, Oreg.), and examined by epifluorescence using a Zeiss microscope equipped with a 63× immersion oil objective. The combination of G546 excitation filer, FT580 dichroic mirror, and LP590 emission filter allowed efficient detection of doxorubicin fluorescence at 590 nm. The fluorescence was detected by a CCD72S camera (Dage-MTI, Inc, Michigan City, Ind.) and images were acquired and analyzed using OPTIMAS software (Optimas Corp., Seattle, Wash.). The fluorescence images were digitized on a 255 level gray scale which was linear with respect to fluorescence intensity and, therefore, proportional to the quantity of DOX. Area (A) per fluorescent image, i.e., per cell, and mean gray per image ($M_I$) were measured for at least 20 cells. Mean gray for a background area containing no cell images ($M_B$) was also determined. Fluorescence units (F.U.) per cell were calculated as:

$$F.U. = \frac{\sum [(M_I - M_B) \cdot A]}{\text{number of cells analyzed}}$$

Fluorescence excitation and emission spectra of DOX and GLU-DOX were obtained using a Shimadzu Model RF-5000 spectroflurophotometer. DOX and GLU-DOX were compared by ascending chromatography on precoated silica gel sheets (Brinkman Instruments, Inc., Westbury, N.Y.) in a chloroform:methanol:phosphate buffer (0.067M, pH 7.0) solvent system (130:60:10).

Fluorescence emission and excitation spectra of GLU-DOX (100:1) were essentially the same as those of unmodified DOX with excitation (absorption) maxima at 501 nm (major) and 534 nm (minor) and emission maxima at 551 nm and 584 nm. Quantum yield appeared to be unaffected by glutaraldehyde derivatization. The $R_f$ of DOX and GLU-DOX in the solvent system employed was 0.53 and 0.86, respectively.

Figure 4A:
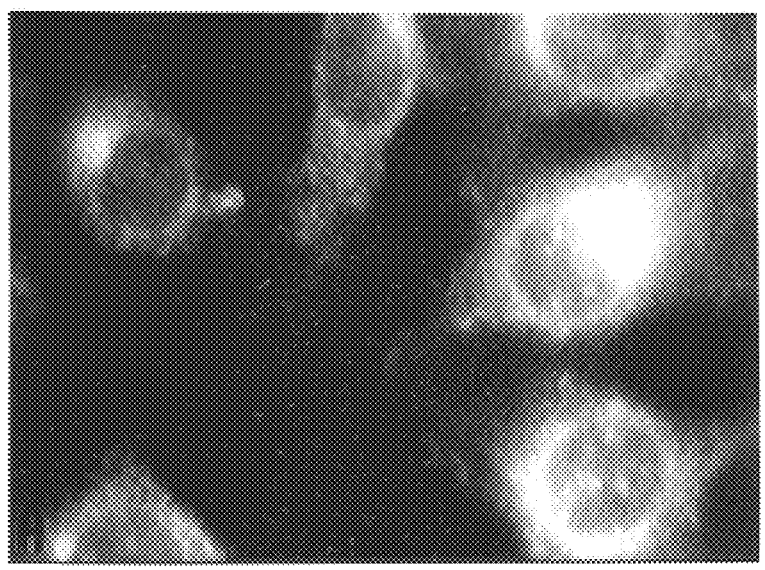
FIG. 4A is a photomicrograph showing the intracellular distribution of doxorubicin fluorescence after a 3 hour DOX exposure. L929 cells were exposed to 5 µg/ml DOX
Figure 4B:
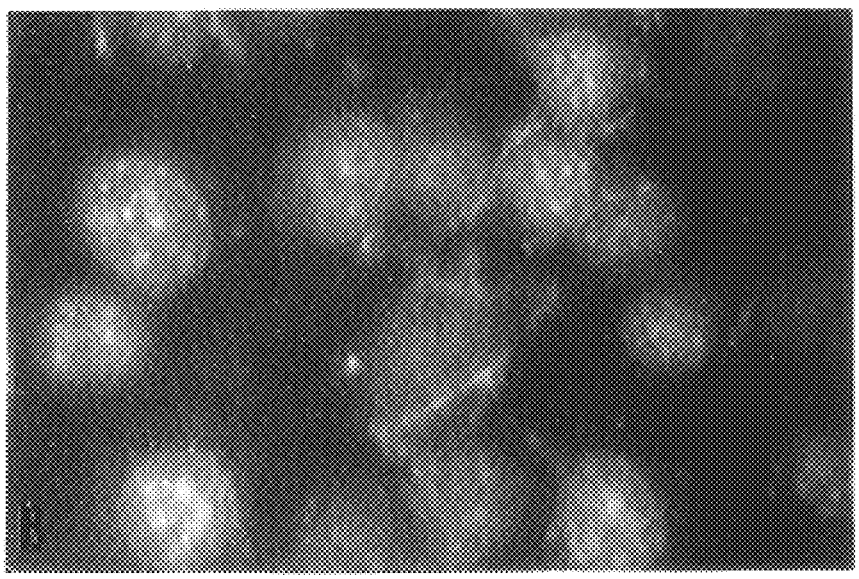
FIG. 4B is a photomicrograph showing the intracellular distribution of DOX fluorescence after a 3 hour DOX exposure and a 2 hour drug-free medium chase period.
Figure 4C:
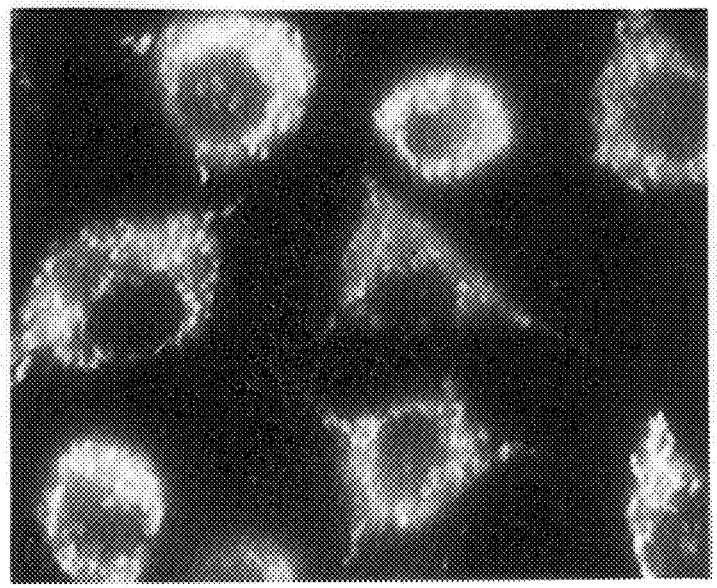
FIG. 4C is a photomicrograph demonstrating the intracellular distribution of GLU-DOX. L929 cells were exposed to 5 µg/ml GLU-DOX for 3 h at 37° C. The GLU-DOX was prepared at 100:1 glutaraldehyde:DOX molar ratio.
Figure 4D:
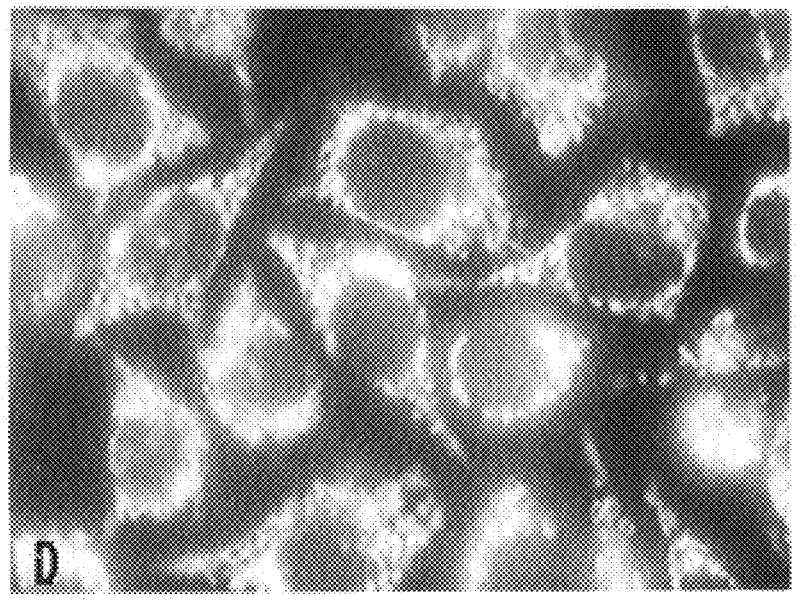
FIG. 4D is a photomicrograph showing the intracellular distribution of GLU-DOX fluorescence after a 3 hour GLU-DOX exposure and a 2 hour drug-free medium chase period.

The subcellular distribution of DOX and GLU-DOX were determined by directly detecting fluorescence of the DOX moiety. FIGS. 4A and 4C show the typical distribution of DOX fluorescence in both nucleus and cytoplasm with distinct paranuclear concentration in some cells. In contrast, GLU-DOX exhibits an exclusively cytoplasmic distribution with localization in punctate and serpiginous structures. Quantitative fluorescence measurements (Table 1) showed that DOX and GLU-DOX uptake per cell were similar in amount despite the difference in subcellular distribution. After a 2 hr chase in drug-free medium, nearly all DOX was lost from the cytoplasmic compartment although some nuclear fluorescence was still detectable (FIG. 4B). GLU-DOX fluorescence, on the other hand, was only slightly diminished at the end of the 2 hour chase period (FIG. 4D) and was still clearly evident even after an 18 hr chase period.

Figure 5A:
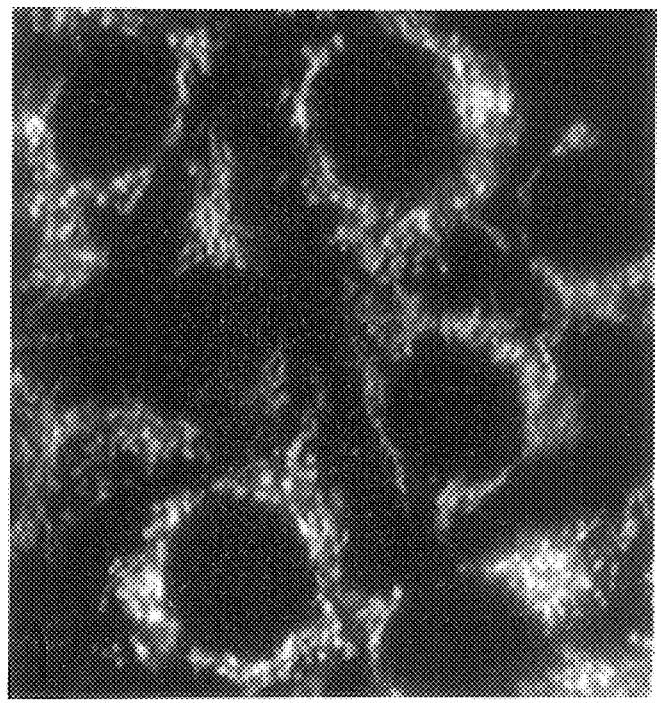
FIG. 5A shows the intracellular distribution of GLU-DOX fluorescence. L929 cells were exposed to 5 µg/ml GLU-DOX prepared at 100:1 glutaraldehyde:DOX molar ratio for 2 h prior to examination by fluorescence microscopy and capture of digitalized images.
Figure 5B:
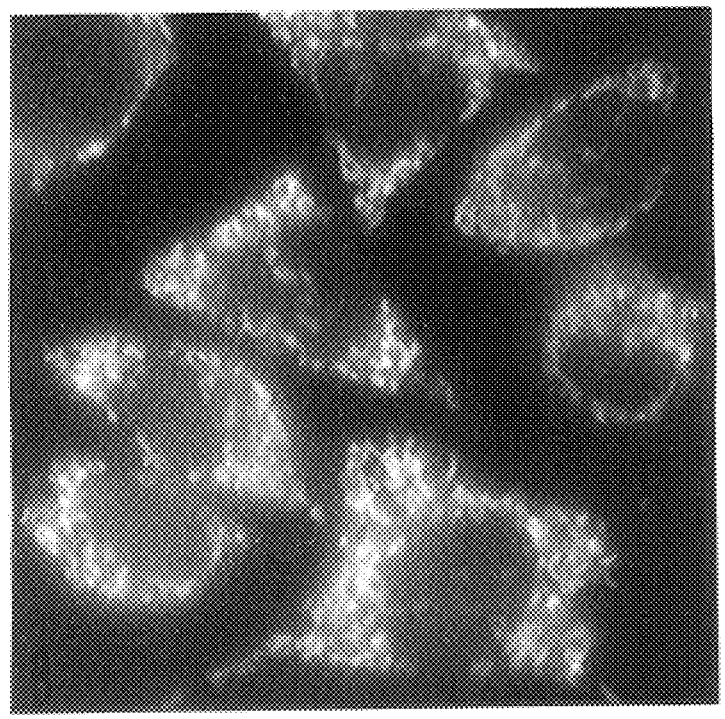
FIG. 5B shows the intracellular distribution of rhodamine 123 fluorescence. L929 cells were exposed to 10 µg/ml rhodamine 123 for 2 h prior to examination by fluorescence microscopy and capture of digitalized images.

The intracellular distribution of GLU-DOX and rhodamine 123 fluorescence is shown in FIGS. 5A and 5B. The pattern of localization in well-defined cytoplasmic structures is strikingly similar for both fluorophores suggesting that GLU-DOX is concentrated in mitochondria. This distribution differs from that DOX and, without wishing to be bound by theory, may be related to the enhanced cytotoxicity of GLU-DOX. For example, concentration and prolonged retention of DOX in the immediate vicinity of the cellular NADPH-generating machinery would be expected to facilitate generation of cytotoxic free radicals.

TABLE 1

Uptake of Doxorubicin (DOX) and Glutaraldehyde-Modified-Doxorubicin (GLU-DO X) by L929 Cells

| Condition | Mean Fluorescence Units per Cell Drug Exposure (5 μg/ml) | |
|---|---|---|
|  | DOX | GLU-DOX |
| 3 h at 37° C. | 124 ± 29 | 149 ± 32 |
| +2 h chase | 18 ± 6 | 127 ± 20 |

What is claimed is:

1. A compound produced by a process comprising the steps of:

admixing glutaraldehyde and a parent cancer chemotherapeutic agent with a reactive amino moiety to produce a reaction mixture; and reacting ethanolamine with said reaction mixture.

2. The compound of claim 1, wherein said parent cancer chemotherapeutic agent with a reactive amino moiety is an anthracycline cancer chemotherapeutic agent.

3. The compound of claim 2, wherein said anthracycline cancer chemotherapeutic agent is selected from the group consisting of doxorubicin, daunorubicin, idarubicin, epirubicin, esorubicin, iododoxorubicin, and pirarubicin.

4. The compound of claim 3, wherein said anthracycline cancer chemotherapeutic agent is doxorubicin.

5. A method for treating a subject suffering from a tumor which comprises administering an effective amount of a compound of claim 1 to said subject for decreasing the size or rate of growth of said tumor.

6. A method for treating a subject suffering from a tumor which comprises administering an effective amount of a compound of claim 2 to said subject for decreasing the size or rate of growth of said tumor.

7. A method for treating a subject suffering from a tumor which comprises administering an effective amount of a compound of claim 3 to said subject for decreasing the size or rate of growth of said tumor.

8. A method for treating a subject suffering from a tumor which comprises administering an effective amount of a compound of claim 3 to said subject for decreasing the size or rate of growth of said tumor.

9. The method of claim 5, wherein said effective amount is between about 0.1 and 10 mg per square meter of surface area of said subject.

10. The method of claim 6, wherein said effective amount is between about 0.1 and 10 mg per square meter of surface area of said subject.

11. The method of claim 7, wherein said effective amount is between about 0.1 and 10 mg per square meter of surface area of said subject.

12. The method of claim 8, wherein said effective amount is between about 0.1 and about 10 mg per square meter of said subject's surface area and wherein said compound is administered intravenously.

13. The method of claim 8, wherein said tumor is a bladder tumor, wherein said effective amount is between about 0.1 and 10 mg per dose, and wherein said compound is administered intravesically.

14. A method for synthesizing a glutaraldehyde-modified cancer chemotherapeutic agent which comprises:
   a) admixing a reactive amino group-containing cancer chemotherapeutic agent with glutaraldehyde, wherein the ratio of said glutaraldehyde to said cancer chemotherapeutic agent is between about 2.5:1 and 100:1, to provide a reaction mixture;
   b) adding ethanolamine to said reaction mixture, wherein the amount of said ethanolamine is effective in reacting with aldehyde moieties of said glutaraldehyde that have not reacted with an amine moiety of said cancer chemotherapeutic agent.

15. The method of claim 14, wherein said reactive amino group-containing cancer chemotherapeutic agent is selected from the group consisting of doxorubicin, daunorubicin, idarubicin, epirubicin, esorubicin, iododoxorubicin, and pirarubicin.

16. The method of claim 15 wherein said reactive amino group-containing cancer chemotherapeutic agent is doxorubicin.

17. The method of claim 5, wherein said tumor is resistant to said parent chemotherapeutic agent.

18. The method of claim 8, wherein said tumor is resistant to doxorubicin.

19. The method of claim 14, wherein said ethanolamine is present in said reaction mixture at a concentration of about 5 to about 100 mM.

* * * * *